US006916334B2

(12) United States Patent
Noonan

(10) Patent No.: US 6,916,334 B2
(45) Date of Patent: Jul. 12, 2005

(54) THERMAL PACK FOR THE FEMALE BREAST

(75) Inventor: Whitney W. Noonan, Duluth, GA (US)

(73) Assignee: Maternal Care, Inc., Alpharetta, GA (US)

( * ) Notice: Subject to any disclaimer, the term of this patent is extended or adjusted under 35 U.S.C. 154(b) by 0 days.

(21) Appl. No.: 10/672,132

(22) Filed: Sep. 26, 2003

(65) Prior Publication Data

US 2005/0070980 A1 Mar. 31, 2005

(51) Int. Cl.$^7$ .................................................. A61F 7/10
(52) U.S. Cl. ........................................ 607/108; 607/114
(58) Field of Search ........................... 607/108–112, 114

(56) References Cited

U.S. PATENT DOCUMENTS

| 5,050,595 | A | * | 9/1991 | Krafft ........................... 607/108 |
| 5,304,215 | A | | 4/1994 | MacWhinnie et al. | |
| 5,409,500 | A | * | 4/1995 | Dyrek ........................... 607/111 |
| 5,897,580 | A | * | 4/1999 | Silver ........................... 607/108 |
| 6,083,254 | A | * | 7/2000 | Evans ........................... 607/96 |
| 2003/0073930 | A1 | | 4/2003 | Morrissey et al. | |

* cited by examiner

Primary Examiner—Roy D. Gibson
Assistant Examiner—Aaron Roane
(74) Attorney, Agent, or Firm—Sutherland Asbill & Brennan LLP

(57) ABSTRACT

A thermal pack is provided for application to a female breast for therapeutic application of heat or cold to the breast, comprises a pliable, disk-shaped body having an aperture extending approximately through the center of the body, the body comprising a top wall having an outer surface and an inner surface, an opposed bottom wall having an outer surface and an inner surface, wherein the inner surface of the top wall and the inner surface of the bottom wall define at least one fluid tight cavity therebetween; and a thermal fluid, such as a gel, contained in the at least one cavity. The thermal pack may have a single cavity wherein the body further comprises two or more baffles which restrict the flow of fluid through to keep the thermal fluid dispersed substantially uniformly in each cavity region between the baffles when the thermal pack is secured against the breast.

20 Claims, 2 Drawing Sheets

THERMAL PACK FOR THE FEMALE BREAST

BACKGROUND OF THE INVENTION

This invention is generally in the field of thermal packs for heat or cold therapy for the female breast.

Commercially available thermal packs are generically provided in shapes and dimensions for use on a variety of body surfaces, to treat a variety of common ailments such as soreness and swelling associated with muscle strain or fatigue. These thermal packs, however, are neither designed for, nor optimal for use on, the female breast.

While breastfeeding or weaning, women may likely experience engorgement, plugged ducts, and even mastitis. These conditions often cause pain, swelling, soreness, and general discomfort in the breasts. One effective treatment of these conditions is the use of a heating pad or cooling pad. Lactation consultants have even been known to suggest using bags of frozen peas wrapped in a thin dishtowel as a cooling pad. U.S. Pat. No. 5,304,215 to Mac Whinnie et al. discloses a thermal heat pack for breast. However, it necessarily covers the nipple, which can rub against and irritate sensitive nipple tissue. These examples and other conventional thermal packs have numerous deficiencies. For example, they may cover and irritate the nipple, may not have sufficient surface for effectively treating the breasts, are too hard or rough in contact with tender breast tissues, and/or cannot be readily and discreetly worn by the woman inside her bra if desired. It would therefore be desirable to provide a new and improved thermal packs that overcome these drawbacks and limitations.

SUMMARY OF THE INVENTION

A thermal pack and methods of use are provided for application to a female breast for therapeutic application of heat or cold to the breast.

In one aspect, the thermal pack comprises (1) a pliable, disk-shaped body having an aperture extending approximately through the center of the body, the body comprising a top wall having an outer surface and an inner surface, an opposed bottom wall having an outer surface and an inner surface, wherein the inner surface of the top wall and the inner surface of the bottom wall define at least one fluid tight cavity therebetween; and (2) a thermal fluid contained in the at least one cavity. In one embodiment, the thermal pack has a single cavity wherein the body further comprises two or more baffles that restrict the flow of fluid through the cavity. For example, each baffle can comprise an area of the inner surface of the top wall bonded to an area of the inner surface of the bottom wall. In one specific embodiment, the thermal pack has four baffles in a spaced relation to one another around the body. In one specific embodiment, each baffle extends from an outer edge of the body towards the aperture.

In one embodiment, the thermal pack further includes a fabric substantially covering the outer surface of the top wall, the outer surface of the bottom wall, or both. For example, the fabric can be a washable hypoallergenic fabric that covers only the outer surface of the top wall.

In a preferred embodiment, the thermal fluid comprises a gel. For example, the gel can be one that comprises an absorbent cross-linked sodium polymer and water.

In one embodiment, the top wall, the bottom wall, or both comprise a thermoplastic polymer film. For example, the polymer film can be a polyolefin, such as a polyethylene or a polypropylene. The top wall and the bottom wall, in one embodiment, each comprise a polymer film and are heat sealed together at their corresponding edges.

In one embodiment, the disk-shaped body is substantially circular. For example, the diameter of the body could be between four and seven inches. In one embodiment, the aperture is substantially circular. For example, the diameter of the aperture could be between one-half inch and three inches.

In a preferred embodiment, the thermal pack comprises (1) a pliable, circular body having an circular aperture extending through the center of the body, the body comprising a top wall having an outer surface and an inner surface, an opposed bottom wall having an outer surface and an inner surface, wherein the inner surface of the top wall and the inner surface of the bottom wall define a fluid tight cavity therebetween, the top wall and the bottom wall each being formed of a polyolefin film; (2) a thermal fluid which comprises a cross-linked polymer gel contained in the cavity; and (3) two or more baffles which restrict the flow of fluid through the cavity to keep the thermal fluid dispersed substantially uniformly in each cavity region between the baffles when the thermal pack is applied to the breast. Preferably, this thermal pack further comprises a fabric substantially covering the outer surface of the top wall, the outer surface of the bottom wall, or both.

In another aspect, a kit is provided which is comprised of a pair of the thermal packs described herein.

In another aspect a method is provided for therapeutic application of heat or cold to a female breast. For example, the method can comprises (1) heating or cooling a thermal pack which comprises a pliable, disk-shaped body having an aperture extending approximately through the center of the body, the body comprising a top wall having an outer surface and an inner surface, an opposed bottom wall having an outer surface and an inner surface, wherein the inner surface of the top wall and the inner surface of the bottom wall define at least one fluid tight cavity therebetween, and a thermal fluid contained in the at least one cavity; and (2) securing the heated or cooled thermal pack against the female breast with the nipple positioned within the aperture. In one embodiment of the method, the body of the thermal pack is circular, the aperture is circular, the top wall and the bottom wall each are formed of a polyolefin film, and the thermal fluid comprises a cross-linked polymer gel. In a further embodiment of the method, the body of the thermal pack further comprises two or more baffles which restrict the flow of fluid through the cavity to keep the thermal fluid dispersed substantially uniformly in each cavity region between the baffles when the thermal pack is secured against the breast.

DETAILED DESCRIPTION OF THE INVENTION

An improved pliable thermal pack has been developed specifically for application to a female breast for therapeutic application of heat or cold to the breast. The thermal pack provides a large outer surface area for contacting the breast, but includes a nipple aperture to avoid rubbing against and irritating the nipple. Preferably, the pack includes a large quantity of thermal gel and has a soft medical fabric covering to enhance user comfort. The thermal pack is lightweight and can be used by itself or can be slipped easily into most sizes of bras.

Advantageously, the thermal pack described herein can help soothe pain, relieve soreness, encourage milk flow, and enhance the overall breastfeeding experience for the woman. The thermal pack also can be used in other therapeutic applications. For example, it can be used to provide soothing relief for post-operative patients recovering from breast surgery, such as reduction or augmentation, biopsy, etc. While not specifically tailored to other areas of the body, the devices can be applied to non-breast tissues for other common, minor discomforts.

The thermal pack described herein preferably is reusable, that is, it can be heated, or cooled, and used tens or hundreds of times. Accordingly, the thermal pack preferably is washable and can be easily cleaned, e.g., by hand with a mild soap/detergent and warm water or by running them through the top rack of a dishwasher washed on a gentle cycle.

Figure 1:
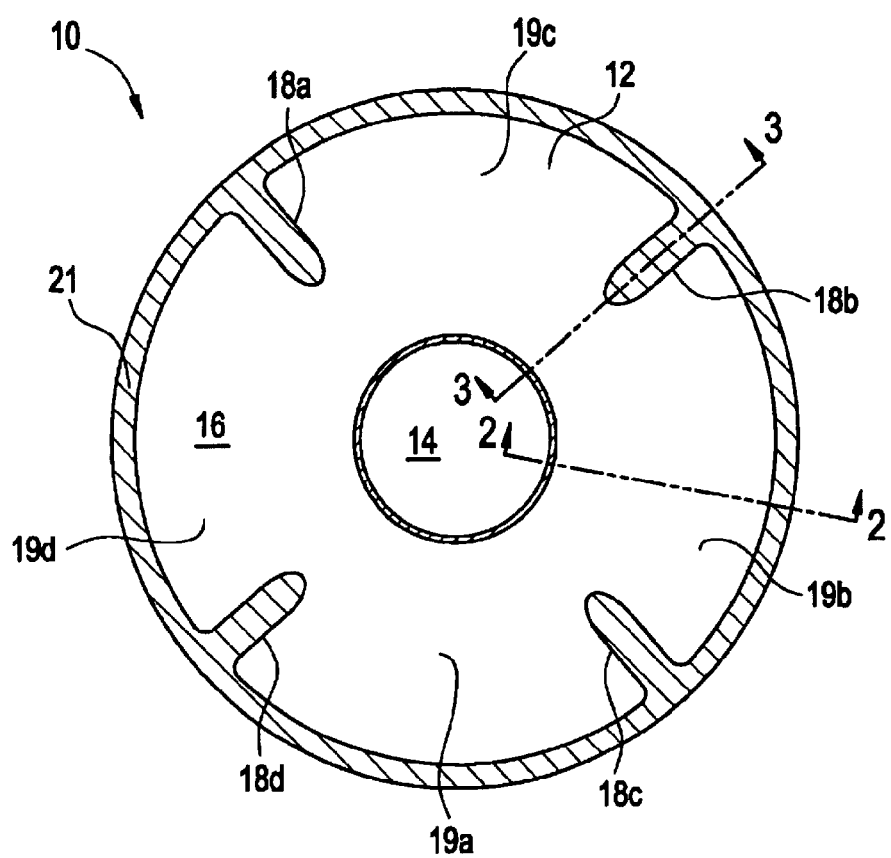
FIG. 1 is plan view of one embodiment of the thermal pack.
Figure 2:
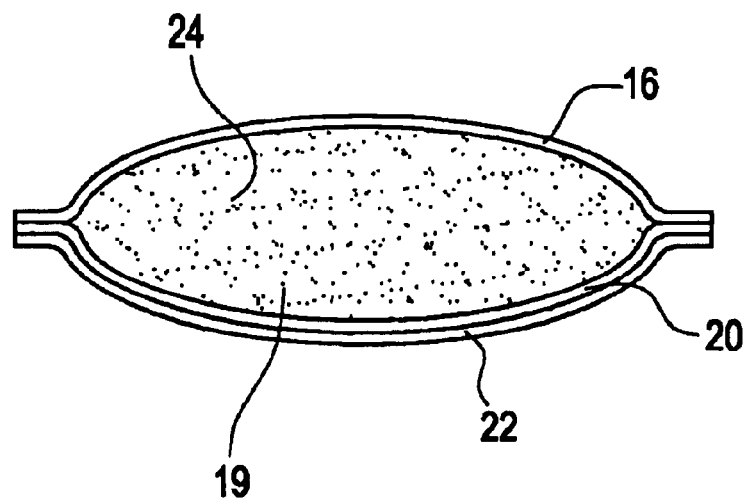
FIG. 2 is a cross-sectional view of the thermal pack shown in FIG. 1, taken along line 2.
Figure 3:
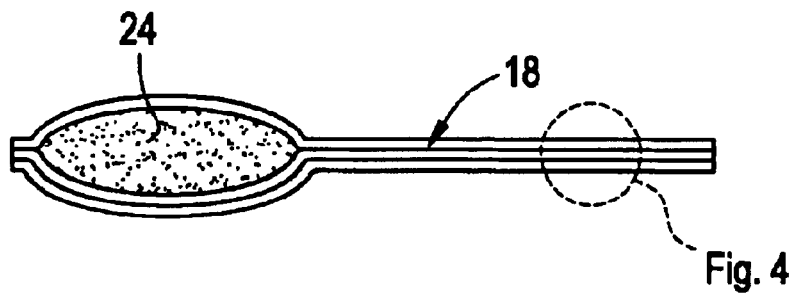
FIG. 3 is a cross-sectional view of the thermal pack shown in FIG. 1, taken along line 3.
Figure 4:
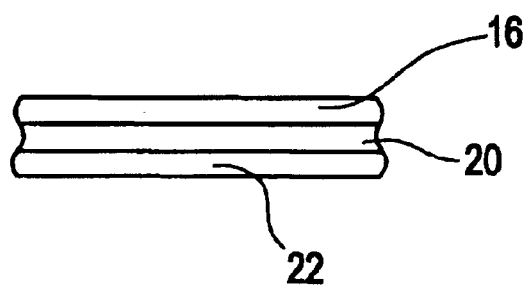
FIG. 4 is a close up of the cross-sectional view of FIG. 3, showing the top wall, bottom wall, and fabric covering at the bottom wall.

The thermal pack can be further understood with reference to the exemplary, non-limiting, embodiment illustrated in FIGS. 1–4.

One embodiment of the thermal pack is illustrated FIGS. 1–4. The thermal pack 10 includes a pliable, disk-shaped body 12 having an aperture 14 extending approximately through the center of the body 12. The body comprises a top wall 16 having an outer surface and an inner surface, and an opposed bottom wall 20 having an outer surface and an inner surface. A fluid tight cavity 19 is disposed between the inner surface of the top wall 16 and the inner surface of the bottom wall 20. A thermal fluid 24 is contained in the cavity 19. Baffles 18a, 18b, 18c, and 18d are provided in the cavity 19 to restrict the flow of thermal fluid in the cavity in order to keep the thermal fluid 24 dispersed substantially uniformly in each cavity region 19a, 19b, 19c, and 19d between the baffles when the thermal pack is applied to the breast. Each baffle extends from an outer edge 21 of the body 12 towards the aperture 14. In this embodiment, each baffle 18 comprises an area of the inner surface of the top wall 16 bonded to an area of the inner surface of the bottom wall 20. The bottom wall 20 is covered by a soft fabric material 22, for contact with the breast.

The pliable, disk-shaped body should be shaped and sized for conformation with the female breast, while simultaneously the aperture should be sized, positioned, and shaped to avoid covering the nipple. In one embodiment, both the body and aperture are substantially circular. In preferred embodiments, the diameter of the body is between about four and about seven inches. In preferred embodiments, the diameter of the aperture is between about one-half inch and about three inches.

The number, size, and placement of the baffles is selected to keep the thermal fluid dispersed substantially uniformly throughout the cavity in order to uniformly transfer heat/cold around the breast. The baffles and the viscosity of the thermal fluid affect how easily the fluid flows under the influence of gravity toward, and accumulates along, the lower edge of the body when applied against the breast. The baffles can vary widely in number, position, and form. For example, there may be between one and ten baffles. As another example, the baffles can extend from the outer edge of the body, from the aperture edge, or a combination thereof. Alternatively, the baffles may be provided in the central region of the cavity without connecting to either edge. Manufacturing considerations also impact baffle design selection. For example, the design should permit ready filling of the cavity with thermal fluid.

A variety of thermal fluids can be used the thermal pack described herein, including ones known in the art. The thermal fluid preferably is one that is biocompatible, non-toxic. In a preferred embodiment, the thermal fluid comprises a gel. Representative examples of gels are those based on the gelation of xanthan gum, locust bean gum, gum tragacanth, guar gum, hydroxypropyl methylcellulose, absorbent polymers, and the like. For example, the gel may be based on a high molecular weight polyacrylic acid cross-linked with a polyalkenyl ether. In one embodiment, the gel comprises an absorbent cross-linked sodium polymer and water. Preferably, the gel is one that can repeatedly heated and cooled, with no appreciable decrease in performance.

The shell of the body, that is the top wall and the bottom wall that define the cavity, is formed of a flexible, pliable material. In a preferred embodiment, the walls are formed from a thermoplastic polymer film. Examples of suitable thermoplastic films include polyolefins, such as polyethylenes and polypropylenes. In a preferred embodiment, the top wall and the bottom wall are heat sealed together at their corresponding outer edges and aperture edges and in the areas defining the baffles.

The fabric covering provides a soft surface for contacting the breast. It can cover all or part of the body. It preferably is a hypoallergenic, medical fabric. The fabric preferably is washable and reusable. The fabric can be made from a variety of woven or non-woven, natural fibers (e.g., cotton, silk) or synthetic fibers (e.g., a polyolefin or polyolefin blend) known in the art. The fabric should be reasonably conductive of heat enough so as not to provide too much of an insulating effect that would interfere with the heat or cold therapy. The fabric covering can be permanently bonded to the body, or alternatively it can be selectively removable/separable from the body of the thermal pack.

In one embodiment, the thermal packs are provided and packaged in pairs, with two thermal packs to a kit.

The preferred use of the thermal pack described herein is in the therapeutic application of heat or cold to a female breast. For example, for warm therapy, the thermal pack can be placed in a microwave oven for a few seconds (e.g., 10 to 20 sec.), removed from the oven, and then gently massaged to mix the thermal fluid and even out any temperature variations throughout the thermal pack. Alternatively, the thermal pack could be heated by immersion in warm (preferably not boiling) water for several minutes (e.g., 5 to 10 min.), removed from the water, and dried. The temperature should be carefully checked and the thermal pack additionally heated or allowed to cool until the desired temperature is reached. For cold therapy, the thermal pack can be placed in a refrigerator until the thermal pack reaches the desired coolness, typically in 30 to 60 minutes. Once the thermal pack is warmed or cooled to the desired temperature, the thermal pack is placed against the breast with the nipple positioned within the aperture. The thermal packs can be held in place manually or can be inserted into a bra the patient is wearing.

Heat therapy or cold therapy for breasts can be indicated for a number of conditions, particularly those associated with breastfeeding and postoperative breast surgery.

Therapy with the thermal pack described herein can aid in the reduction of swelling and soreness associated with engorgement, can encourage milk flow, can help in the treatment of mastitis, can aid in dilation of plugged milk ducts, can assist with milk letdown, and can comfort weaning breasts. The thermal pack also can be used to provide soothing relief for post-operative patients recovering from breast surgery, such as reduction or augmentation. While not specifically tailored to other areas of the body, the devices can be applied to non-breast tissues for other common, minor discomforts.

Modifications and variations of the methods and devices described herein will be obvious to those skilled in the art from the foregoing detailed description. Such modifications and variations are intended to come within the scope of the appended claims.

I claim:

1. A thermal pack for application to a female breast for therapeutic application of heat or cold to the breast comprising:
    a pliable, disk-shaped body having an aperture extending approximately through the center of the body, the body comprising
        a top wall having an outer surface and an inner surface, an opposed bottom wall having an outer surface and an inner surface, wherein the inner surface of the top wall and the inner surface of the bottom wall define a single fluid tight cavity therebetween;
    two or more baffles which impede the flow of fluid within the cavity; and
    a thermal fluid contained in the cavity, wherein the cavity extends completely around the aperture.

2. The thermal pack of claim 1, wherein each baffle comprises an area of the inner surface of the top wall bonded to an area of the inner surface of the bottom wall.

3. The thermal pack of claim 2, having four baffles in a spaced relation to one another around the body.

4. The thermal pack of claim 1, wherein each baffle extends from an outer edge of the body toward the aperture.

5. The thermal pack of claim 1, further comprising a fabric substantially covering the outer surface of the top wall, the outer surface of the bottom wall, or both.

6. The thermal pack of claim 5, wherein the fabric is a washable hypoallergenic fabric and covers only the outer surface of the top wall.

7. The thermal pack of claim 1, wherein the thermal fluid comprises a gel.

8. The thermal pack of claim 7, wherein the gel comprises an absorbent cross-linked sodium polymer and water.

9. The thermal pack of claim 1, wherein the top wall, the bottom wall, or both comprise a thermoplastic polymer film.

10. The thermal pack of claim 9, wherein the polymer film comprises polyethylene or polypropylene.

11. The thermal pack of claim 9, wherein the top wall and the bottom wall each comprise a polymer film and are heat-sealed together at their corresponding edges.

12. The thermal pack of claim 1, wherein the disk-shaped body is substantially circular.

13. The thermal pack of claim 12, wherein the diameter of the body is between four and seven inches.

14. The thermal pack of claim 1, wherein the aperture is substantially circular.

15. The thermal pack of claim 14, wherein the diameter of the aperture is between one-half inch and three inches.

16. A kit comprised of parts comprising:
    two of the thermal packs according to claim 1.

17. A thermal pack for application to a female breast for therapeutic application of heat or cold to the breast comprising:
    a pliable, circular body having an circular aperture extending through the center of the body, the body comprising
        a top wall having an outer surface and an inner surface, an opposed bottom wall having an outer surface and an inner surface, wherein the inner surface of the top wall and the inner surface of the bottom wall define a single fluid tight cavity therebetween, the top wall and the bottom wall each being formed of a polyolefin film;
    a thermal fluid which comprises a cross-linked polymer gel contained in the single cavity; and
    two or more baffles which impede the flow of fluid within the single cavity to keep the thermal fluid dispersed substantially uniformly in each cavity region between the baffles when the thermal pack is applied to the breast, wherein the cavity extends completely around the aperture.

18. The thermal pack of claim 17, further comprising a fabric substantially covering the outer surface of the top wall, the outer surface of the bottom wall, or both.

19. A method for therapeutic application of heat or cold to a female breast, the method comprising:
    heating or cooling a thermal pack which comprises a pliable, disk-shaped body having an aperture extending approximately through the center of the body, the body comprising a top wall having an outer surface and an inner surface, an opposed bottom wall having an outer surface and an inner surface, wherein the inner surface of the top wall and the inner surface of the bottom wall define a single fluid tight cavity therebetween, two or more baffles which impede the flow of fluid within the cavity, and a thermal fluid contained in the cavity; and
    securing the heated or cooled thermal pack against the female breast with the nipple positioned within the aperture, wherein the cavity extends completely around the aperture.

20. The method of claim 19, wherein the body of the thermal pack is circular, the aperture is circular, the top wall and the bottom wall each are formed of a polyolefin film, the thermal fluid comprises a cross-linked polymer gel.

* * * * *